United States Patent
Nichols et al.

(10) Patent No.: US 9,839,491 B2
(45) Date of Patent: Dec. 12, 2017

(54) DENTAL HANDPIECES

(71) Applicant: CAO Group, Inc., West Jordan, UT (US)

(72) Inventors: Jack Nichols, American Fork, UT (US);
Robert Larsen, Riverton, UT (US);
Bruce Draper, Sandy, UT (US);
Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 73 days.

(21) Appl. No.: 14/475,228

(22) Filed: Sep. 2, 2014

(65) Prior Publication Data

US 2016/0058525 A1     Mar. 3, 2016

(51) Int. Cl.
*A61C 3/00*     (2006.01)
*A61C 1/08*     (2006.01)

(52) U.S. Cl.
CPC ........ *A61C 1/088* (2013.01); *A61C 2204/002* (2013.01)

(58) Field of Classification Search
CPC ........................... A61C 1/088; A61C 2204/002
See application file for complete search history.

(56) References Cited

U.S. PATENT DOCUMENTS

| | | | |
|---|---|---|---|
| 4,147,355 A * | 4/1979 | Barlow | F41A 33/02 446/405 |
| 4,208,579 A * | 6/1980 | Scrivo | G02B 6/0006 250/227.22 |
| 4,725,231 A | 2/1988 | Boinot et al. | |
| 5,324,197 A | 6/1994 | Shain et al. | |
| 5,450,293 A * | 9/1995 | Hoffman | A61B 1/07 362/103 |
| 5,487,662 A * | 1/1996 | Kipke | A61C 9/0006 433/215 |
| 5,899,692 A | 5/1999 | Davis et al. | |
| 5,902,105 A | 5/1999 | Uejima et al. | |
| 5,908,295 A | 6/1999 | Kawata et al. | |
| 6,015,290 A | 1/2000 | Rosenstatter | |
| 6,095,810 A | 8/2000 | Bianchetti et al. | |
| 6,161,937 A | 12/2000 | Rosenstatter | |
| 6,319,002 B1 | 11/2001 | Pond | |
| 6,579,093 B2 | 6/2003 | Bailey et al. | |
| 6,769,093 B1 | 7/2004 | Krieger | |
| 7,104,794 B2 | 9/2006 | Levy | |
| 8,371,848 B2 * | 2/2013 | Okawa | A61B 1/24 433/29 |
| 8,435,034 B2 | 5/2013 | Gersh et al. | |
| 8,905,924 B2 * | 12/2014 | Khouri | A61C 1/088 433/29 |
| 2008/0131835 A1 * | 6/2008 | Schatz | A61C 1/088 433/29 |

* cited by examiner

*Primary Examiner* — George Manuel

(57) ABSTRACT

A dental handpiece may comprise a detachable light source assembly comprising a light source, a power source, and at least one switch, and the detachable light source assembly may be configured to be selectively removable from the handpiece.

5 Claims, 5 Drawing Sheets

DENTAL HANDPIECES

TECHNICAL FIELD OF THE INVENTION

The present invention relates to dental instruments or dental handpieces, referred to collectively as dental handpieces. More specifically, the present invention relates to dental handpieces that facilitate illumination of the worksite.

SUMMARY OF THE INVENTION

In some embodiments, a dental handpiece may comprise a detachable light source assembly comprising a light source, a power source, and at least one switch, and the detachable light source assembly may be configured to be selectively removable from the handpiece.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific example embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

DETAILED DESCRIPTION

Figure 1:
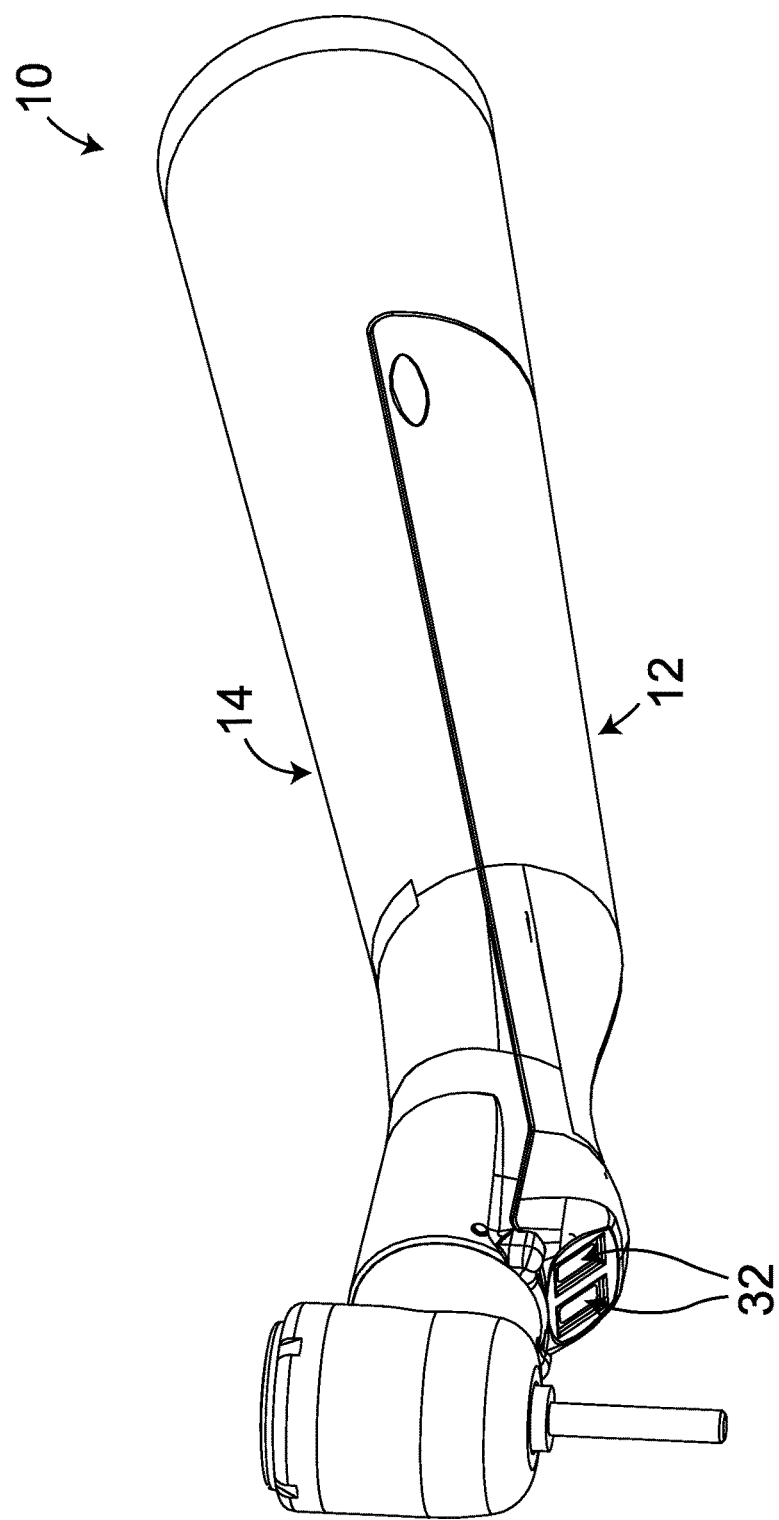
FIG. 1 depicts an isometric view of a handpiece including a detachable light source assembly according to an embodiment of the present invention.

Dental handpieces are hand-held devices, such as drilling devices which may be utilized by dentists or practitioner to drill into a patient's teeth or to otherwise perform dental procedures. The drilling handpiece may be powered by air or electricity or manual power. For the air driven drilling handpiece, which is most commonly used in the practice of dentistry, it typically consists of a steel, metal, and/or plastic assembly that is attached to an external pneumatic pressure source. The air pressure is controlled by a foot pedal and allows for varying air pressure to be introduced into the handpiece. The pressurized air moves a turbine assembly within the handpiece to create a rotating mechanical action. Various types of drill bits, burs, or attachments may be connected to the turbine to perform the desired mechanical action. Additional ancillary functions include the delivery of pressurized water or air-water mix to the attached drill bit, and the inclusion of focused light directed at the tip of the drill bit. By directing the light in this manner, the dentist can not only see the location and behavior of the drill bit relative to the tooth, but this source of light provides illumination to the worksite where the handpiece blocks the light from the overhead operator light.

Traditionally, the methods of providing focused light onto the drill bit has been in the form of optical fiber or light pipes, which receive light generated at a remote source and conduct the light through the air tubing, through the dental handpiece, and to a terminating window or orifice near the turbine assembly that directs the light onto the drill bit. Alternatively, the light may be generated from an intermediate attachment, known as a swivel, which lies between the air tubing and the dental handpiece. In this configuration, electrically conductive wires within the air tubing provide the electrical power to the light source located within the swivel. These technology have been guided and restricted by a number of key performance features that dentists require. First is the ability to clean and sterilize the dental handpiece. This is typically done by autoclave sterilization wherein the article is placed in a chamber where pressurized steam at a temperature of 121-134° C. and pressures of 15-25 psi is generated and allowed to contact the article for a period of time. This action of pressurized steam above the normal boiling point of water acts to destroy all active biologics. Unfortunately, steam at these temperatures is destructive to electrical and electronic components. Further, the repeated use of elevated temperature steam can have a corrosive effect on electrical contacts, limiting the transmission of electricity across such contacts.

A second limitation has been the availability of technology to generate the desired light. Where the only sources light available were tungsten filament or halogen bulbs, this prevented including these bulbs in the handpiece directly because the physical size of bulbs needed to generate the desired light intensity would not allow placing them inside the handpiece itself. Further, such bulbs generate a considerable amount of heat which would make holding the handpiece (made of steel or other metal) uncomfortable at best. Recent advances in light emitting diode (LED) technology have permitted the creation of light sources that are very small and compact, and generate considerably less heat. However, the use of this technology has been hampered by the availability of the desired color and intensity produced by such, coupled with the electronics necessary to power these LEDs and the physical size limitations imposed by the handpiece. Only recently have these light source concerns been addressed with LEDs that are physically small enough to fit directly within the handpiece form, that provide enough light of the desired color to be useful to the dentist, and are able to survive the autoclave process to some extent.

Another limitation is patient safety. Because the handpieces are composed of steel or other metal or plastic, and the drill bits themselves are steel, any electrical connection from the handpiece back to a power source presents to possibility of electricity reaching the patient and causing harm. Even with robust safety circuits, a power surge or failure of the safety circuits could allow for the patient or the dentist to be electrocuted. Thus, any means for electrically powering an integrated light source must be a fully contained power source that is not connected to an electrical outlet. Recent advances in on-board power sources have provided for acceptable, but not ideal, means for providing electrical power. The best of these technologies is a miniature pneumatic generator that uses the pressurized air to generate electricity. However, this technology requires that the handpiece be in operation with the drill turning in order for the light source to receive power.

What is needed is a method to power an integrated light source in a dental handpiece in such a manner that all electrical components are contained within the handpiece, that the generation of light is independent of the pneumatic force used to operate the handpiece, and ideally that all electrical components are easily serviceable without requiring dismantling of the entire handpiece assembly.

Embodiments of the present invention incorporate an illumination light source directly into a dental handpiece, without the use of fiber optics or other optical transmission methods to transmit the light from the point of source to the desired target. A light source for this invention may be a light emitting diode (LED) or multiple LEDs affixed to the handpiece such that the LEDs illuminate directly onto the target. Additional light sources that may be utilized include OLED (organic LED), miniature filament, and/or halogen bulb. The light source can be affixed to the main body of the dental handpiece, or to a portion of the handpiece that is distinct or separable from the main body of the handpiece by construction or by methods of use. The light source may be positioned at a distance from the axis of the drill bit such that illumination of the distal area of the drill bit is optimal. The angle of emission of the mounted light source may be such that the distal area of the drill bit is illuminated, with additional illumination around or below the terminal end of the drill bit also possible. Illumination may be achieved either through one distinct light source, or from multiple light sources positioned at varying distances from the turbine assembly and/or numerous locations (e.g., clock positions) around the perimeter of the drill bit axis.

In further embodiments, a light source may be mounted wholly or partially within the handpiece body, such body incorporating a transparent or optically transmitting member that forms a portion of the handpiece assembly such that the light source illuminates the transparent member and the transparent member then transmits the light to the target area.

One embodiment of this design is an annular transparent member that is ring shaped and that may be concentric with an axis of the drill bit. When the annular transparent member is illuminated by the light source, it may provide a pattern of light that substantially encompasses the perimeter of an affixed drill bit. Accordingly, a portion of the drill bit may be encircled with light. This may provide an enhanced benefit of reducing or eliminating shadows that might occur from light sources that direct light from a single location. The elimination of shadows may be beneficial to the dentist in accurately identifying and observing the tooth structure as it is being worked on.

Embodiments of the current invention include the use of a power source affixed to or within the dental handpiece. A power source for some embodiments may be an electrochemical battery. The electrochemical battery may be designed so that the battery may withstand repeated exposure to the autoclave sterilization process with minimal adverse effect to the battery. For some embodiments, the battery power source may be a lithium-based chemistry that is design to withstand the autoclave process. In additional embodiments, electrochemical chemistries such as zinc-based chemistries, nickel-cadmium, nickel-metal-hydyde, lithium-cobalt, and lithium-iron-phosphate may be utilized.

Power generation devices may also be incorporated into embodiments of the present invention, such as photovoltaic cells or kinetic motion mechanisms. Additionally, capacitors may be utilized in some embodiments.

Some embodiments of the invention include a switch mechanism that allows the operator to select when the light source is active or inactive. The switch provides for a mechanical actuation to complete a circuit from the power source to the light source. Any number of switch styles may be suitable for this purpose such as button, slide, bimetal, thermal, reed, magnetic, or rotational switches.

In some embodiments, the switch may be a motion-sensitive switch that closes the circuit when the switch—and by extension the article it is connected to—is physically moved. Thus, the action of picking up, handling, or operating the dental handpiece may provide sufficient motion to keep the motion-sensitive switch closed and allow for electrical power to operate the light source. Additionally, the handpiece may include electronic components that provide for desired operation of the light source such as limited continued energizing of the light source for a specific period of time after motion of the handpiece has ceased. An important consideration to the selection of the switch and electronic components is the ability to withstand the autoclave process.

Some embodiments of this invention allow for the location and combination of the power source, switch, supporting electronics, and light source(s) into a discrete assembly that forms a portion of the handpiece assembly and is removable from the handpiece as a single unit. By combining these components into a discrete assembly, it allows for modular design and construction of the article and more importantly allows for rapid and simple servicing and/or replacement of these electronic components without the need of dismantling or replacing the handpiece in general. In one embodiment a detachable portion of the handpiece housing includes the electronic components that facilitate the operation of the light source(s), with the arrangement of the components and the position of this detachable portion ideally located within the handpiece such that the light source is optimally positioned relative to the drill bit, and the shape and size of the handpiece is not hindered by the presence of this detachable portion. The detachable portion may be affixed by mechanical fastener, magnets or adhesive such that removal of the detachable portion requires a conscious effort to detach.

The detachable portion, and its components, may be designed such that they may remain affixed to the handpiece during the autoclave cycle, or may be removed from the handpiece assembly to facilitate charging or to prevent the detachable portion from being exposed to the autoclave process. Alternately, the design of the handpiece assembly may be such that multiple detachable portions exist wherein the light source, switch, power source, or any combination of these are isolated into separate detachable portions.

Embodiments of the present invention include devices and methods for externally charging or recharging the internal power source. This can be accomplished through contact points positioned on or within the detachable portion of the dental handpiece, or on or within the fixed portions of the handpiece. Whether attached to the handpiece assembly, or separated from the handpiece assembly as the detached portion, the power source may be placed on or within a charging structure that provides electrical power to the power source. This charging may occur through direct electrical contact with interface pads or leads, or may be accomplished through methods such as indirect electromagnetic induction.

As shown in FIG. 1, a handpiece 10 according to one embodiment of the present invention may include a detachable light source assembly 12 that may be mounted to the main body 14 of the handpiece 10. The main body 14 of the handpiece may include a turbine assembly 16 for receiving and rotating a drill bit 18. The main body 14 may also include an elongate portion 20 that includes internal fluid channels (not shown) for directing air and water through the handpiece 10.

Figure 2:
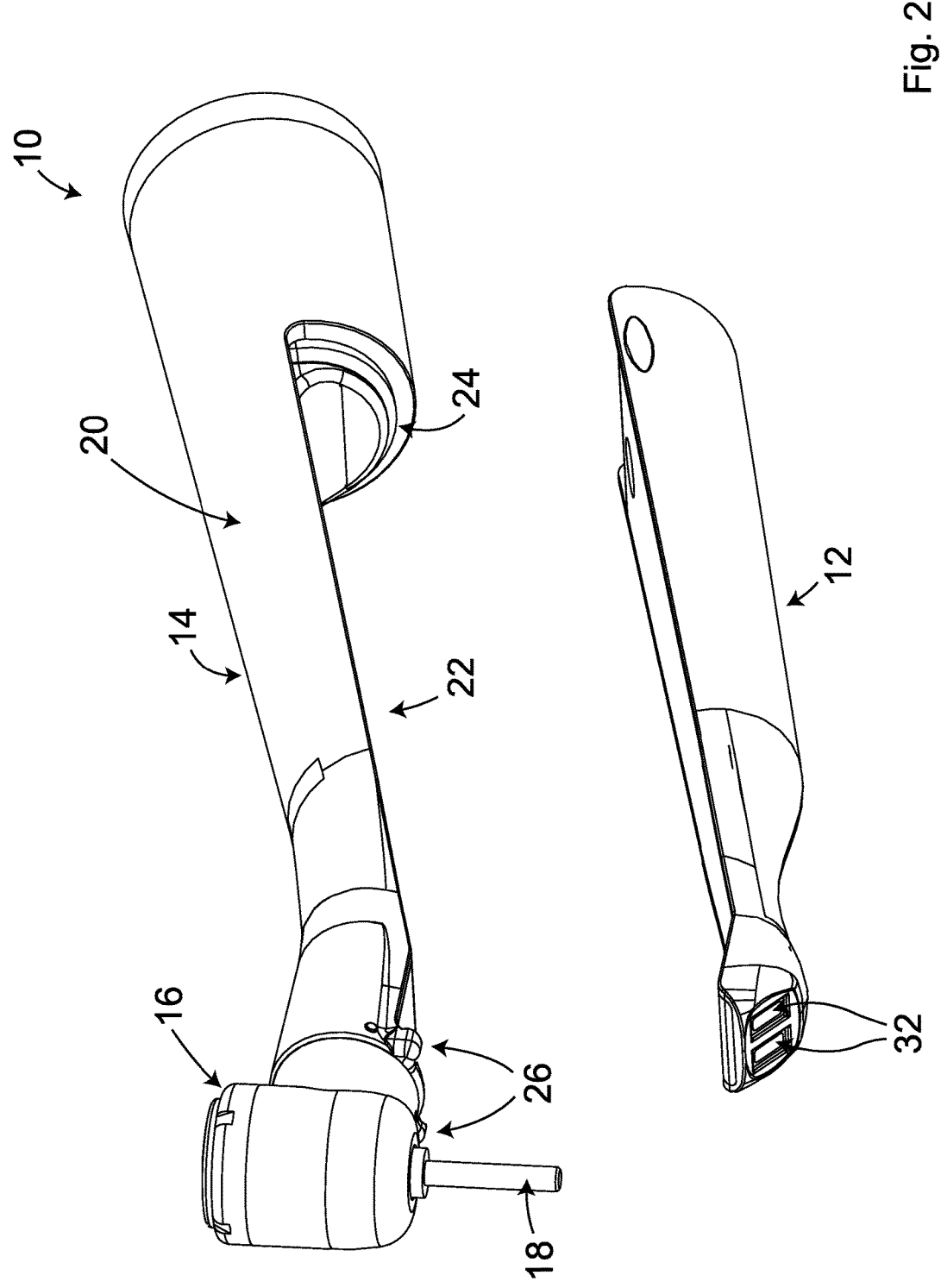
FIG. 2 depicts an exploded view of the handpiece of FIG. 1.

As shown in an exploded view of the handpiece in FIG. 2, the elongate portion 20 of the handpiece 10 may additionally include a receptacle 22 for receiving the detachable light source assembly 12. The receptacle 22 may include positioning features 24, 26 to facilitate positioning the detachable light source assembly 12 on the main body 14 of the handpiece 10 and maintaining the position of the detachable light source assembly 12 relative to the main body 14 of the handpiece 10. A first positioning feature 26 may include protrusions that may prevent lateral movement longitudinal and rotational movement of a first end of the detachable light source assembly relative to the main body 14. A second positioning feature 24 may include a contoured surface that interfaces with a corresponding contoured surface of the detachable light source assembly 12, which may prevent longitudinal and rotational movement of a second end of the detachable light source assembly relative to the main body 14.

Figure 3:
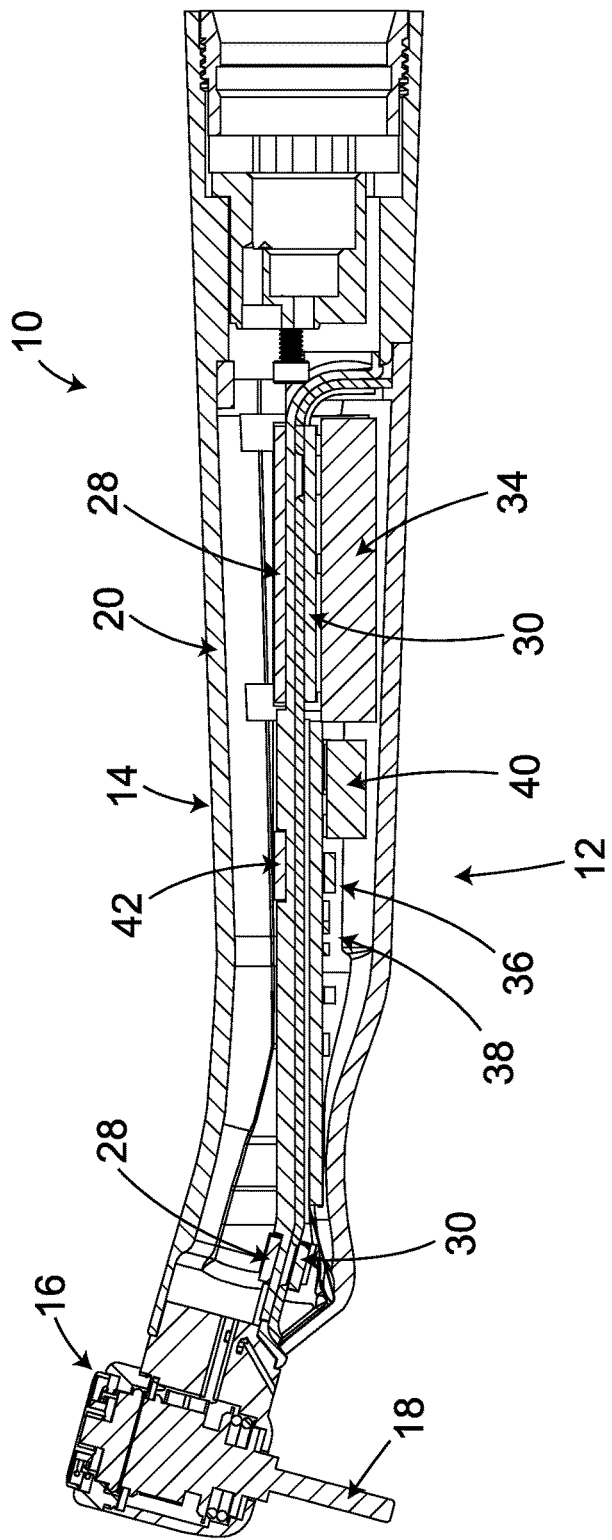
FIG. 3 depicts a cross-sectional view of the handpiece of FIG. 1.

As shown in a cross-sectional view in FIG. 3, magnets 28 may be positioned behind a wall of the receptacle 22 of the main body 14 of the handpiece 10. The magnets 28 may interact with magnets 30 of the detachable light source assembly 12 when the detachable light source assembly 12 is positioned within the receptacle 22 causing a magnetic attraction therebetween, which may retain the detachable light source assembly 12 within the receptacle 22. Accordingly, once the detachable light source assembly 12 is positioned within the receptacle 22 an operator must grip the detachable light source assembly 12 and apply a lateral force sufficient to overcome the magnetic attraction between the magnets 28 and 30 to remove the detachable light source assembly 12 from the main body 14 of the handpiece 10.

The detachable light source assembly 12 may include one or more light sources, such as LEDs 32 (see FIGS. 1 and 2) positioned at the first end to that may direct light toward the drill bit 18 when the detachable light source assembly 12 is installed on the main body 14. Additional electronic components of the detachable light source assembly 12 may include a battery 34, a first switch 36, a second switch 38 and timing electronics 40 (see FIG. 3).

The first switch 36 may be magnetically actuated switch, such as a hall effects switch or reed switch, which may be actuated by the presence of a magnetic field. As shown in FIG. 3, when the detachable light source assembly 12 is installed on the main body 14 a magnet 42 within the main body 14 is positioned proximate to the first switch 36 and may activate the first switch 36.

The second switch 38 may be a motion actuated switch that is activated in response to a change in motion (i.e., an acceleration). Accordingly, the second switch 38 may be activated in response to an operator picking up and using the handpiece 10 with the detachable light source assembly 12 installed thereon.

For a completed circuit between the battery 34 and the LEDs 32, both the first and second switches 36 and 38 must be activated. Thus, when the detachable light source assembly 12 is installed on the main body 14 and the handpiece 10 experiences changes in motion, the LEDs 32 will automatically illuminate. However, when the detachable light source assembly 12 is not installed on the main body 14, the first switch will not be activated and the LEDs 32 will not illuminate in response to handling and movement of the detachable light source assembly 12.

The control electronics 40 may be configured to provide power to the LEDs 32 for a period of time after the first and/or second switches 36 and 38 are deactivated. For example, the control electronics 40 may include a capacitor that may discharge for a period of time after the deactivation of the first and/or second switches 36 and 38. This may provide a continuous illumination from the LEDs 32 while an operator is using the handpiece 10 even though there may be small moments during operation that the handpiece 10 does not move and the second switch 38 may be momentarily deactivated.

Figure 4:
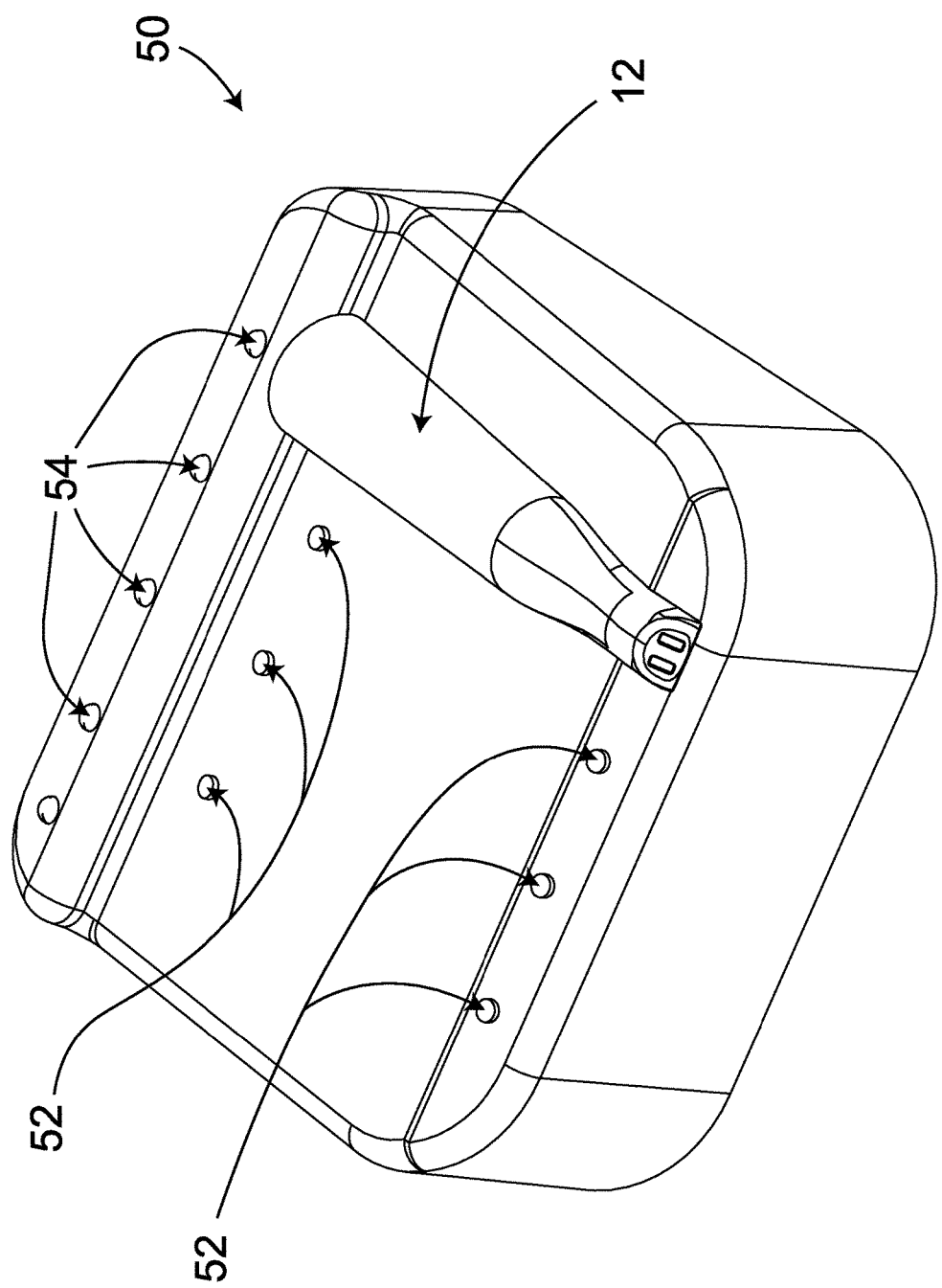
FIG. 4 depicts an isometric view of the detachable light source assembly of the handpiece of FIG. 1 on a charging unit.

As shown in FIG. 4, a charging unit 50 may be utilized to charge the battery 34 of the detachable light source assembly 12. The charging unit 50 may be configured to accommodate multiple detachable light source assemblies 12 and charge them simultaneously. Each bay of the charging unit 50 may include electrodes 52 and a corresponding LED indicator 54, which may indicate a charging status.

Figure 5:
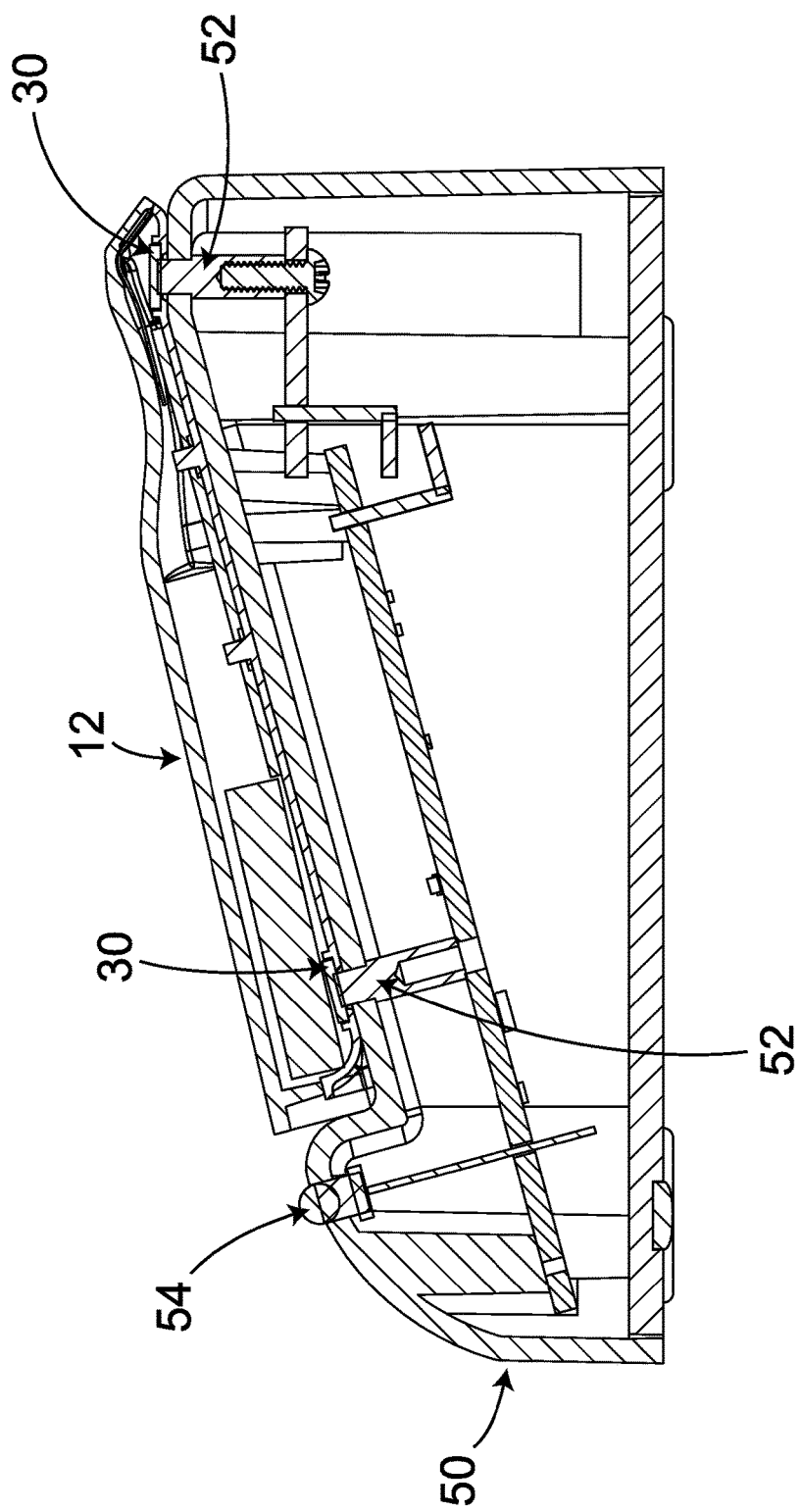
FIG. 5 depicts a cross sectional view of the detachable light source on the charging unit of FIG. 4.

As shown in a cross-sectional view in FIG. 5, each set of electrodes 52 may be positioned to contact a magnet 30 of the detachable light source assembly 12 when the detachable light source assembly 12 is positioned on the charging unit 50. The electrodes 52 may also be magnetic, thus a magnetic attraction between the electrodes 52 and the magnets 30 may retain the detachable light source assembly 12 on the charging unit 50 until a sufficient force is applied to remove the detachable light source assembly 12 from the charging unit 50. The charging unit may provide electric current to the electrodes and the battery 34 may be charged over a period of time and when the battery 34 has been fully charged, the LED indicator 54 may illuminate with a color or blinking pattern that indicates that charging is complete.

The present invention may be embodied in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental handpiece comprising:
    a detachable light source assembly comprising a light source, a power source, and at least one switch;
    wherein the dental handpiece comprises a dental drill;
    wherein the detachable light source assembly is configured to be selectively removable from a receptacle of the dental drill as a single unit;
    wherein the at least one switch comprises a first switch and a second switch;
    wherein a circuit between the light source and the power source is completed only when both the first switch and the second switch are simultaneously activated; and
    wherein the first switch comprises a magnetically activated switch and the second switch comprises a motion activated switch.

2. The dental handpiece of claim 1, wherein the power source comprises a battery.

3. The dental handpiece of claim 1, wherein the detachable light source assembly further comprises control electronics.

4. The dental handpiece of claim 3, wherein the control electronics comprise a capacitor.

5. The dental handpiece of claim 1, wherein the light source comprises at least one LED.

* * * * *